(12) United States Patent
Rogers et al.

(10) Patent No.: US 11,826,049 B2
(45) Date of Patent: Nov. 28, 2023

(54) DEVICES FOR DEPLOYING TISSUE FASTENERS

(71) Applicant: Opus KSD Inc., Pembroke, MA (US)

(72) Inventors: Charles H. Rogers, Halifax, MA (US); Eduard Ulise Milea, Irvine, CA (US); Robert F. Hatch, Pembroke, MA (US); Karl Robert Leinsing, Dover, NH (US); Joseph Mark Durant, Dover, NH (US)

(73) Assignee: Opus KSD Inc., Pembroke, MA (US)

(*) Notice: Subject to any disclaimer, the term of this patent is extended or adjusted under 35 U.S.C. 154(b) by 0 days.

(21) Appl. No.: 18/117,072

(22) Filed: Mar. 3, 2023

(65) Prior Publication Data
US 2023/0285020 A1   Sep. 14, 2023

Related U.S. Application Data

(60) Provisional application No. 63/318,967, filed on Mar. 11, 2022.

(51) Int. Cl.
| | | |
|---|---|---|
| *A61B 17/10* | (2006.01) | |
| *A61B 17/064* | (2006.01) | |
| *A61B 17/08* | (2006.01) | |
| *A61B 17/00* | (2006.01) | |

(52) U.S. Cl.
CPC ............ *A61B 17/10* (2013.01); *A61B 17/064* (2013.01); *A61B 2017/00004* (2013.01); *A61B 2017/081* (2013.01)

(58) Field of Classification Search
CPC .............................. A61B 17/10; A61B 17/064
See application file for complete search history.

(56) References Cited

U.S. PATENT DOCUMENTS

| | | | |
|---|---|---|---|
| 5,292,326 A * | 3/1994 | Green | A61B 17/04 227/181.1 |
| 6,726,705 B2 | 4/2004 | Peterson et al. | |
| 8,506,591 B2 * | 8/2013 | Danielson | A61B 17/064 227/19 |
| 9,232,943 B2 | 1/2016 | Rogers et al. | |
| 10,918,381 B2 | 2/2021 | Guo et al. | |
| 2006/0122635 A1 * | 6/2006 | Naegeli | A61B 17/068 606/142 |
| 2016/0051255 A1 * | 2/2016 | Danielson | A61B 17/0682 606/219 |

* cited by examiner

*Primary Examiner* — Nathaniel C Chukwurah
(74) *Attorney, Agent, or Firm* — Brown Rudnick LLP; Matthew P. York

(57) ABSTRACT

The present invention is directed to a hand-held surgical device, operable by a single user, for deploying fasteners to close a wound or incision in tissue. The device includes tissue pinching and folding members operably controlled by the user during actuation of a trigger of the device, which can temporarily secure and expose inner surfaces of two edges of an incision or wound, where one of a plurality of fasteners can be inserted upon further actuation of the trigger, without crushing or causing undue trauma to the tissue.

27 Claims, 15 Drawing Sheets

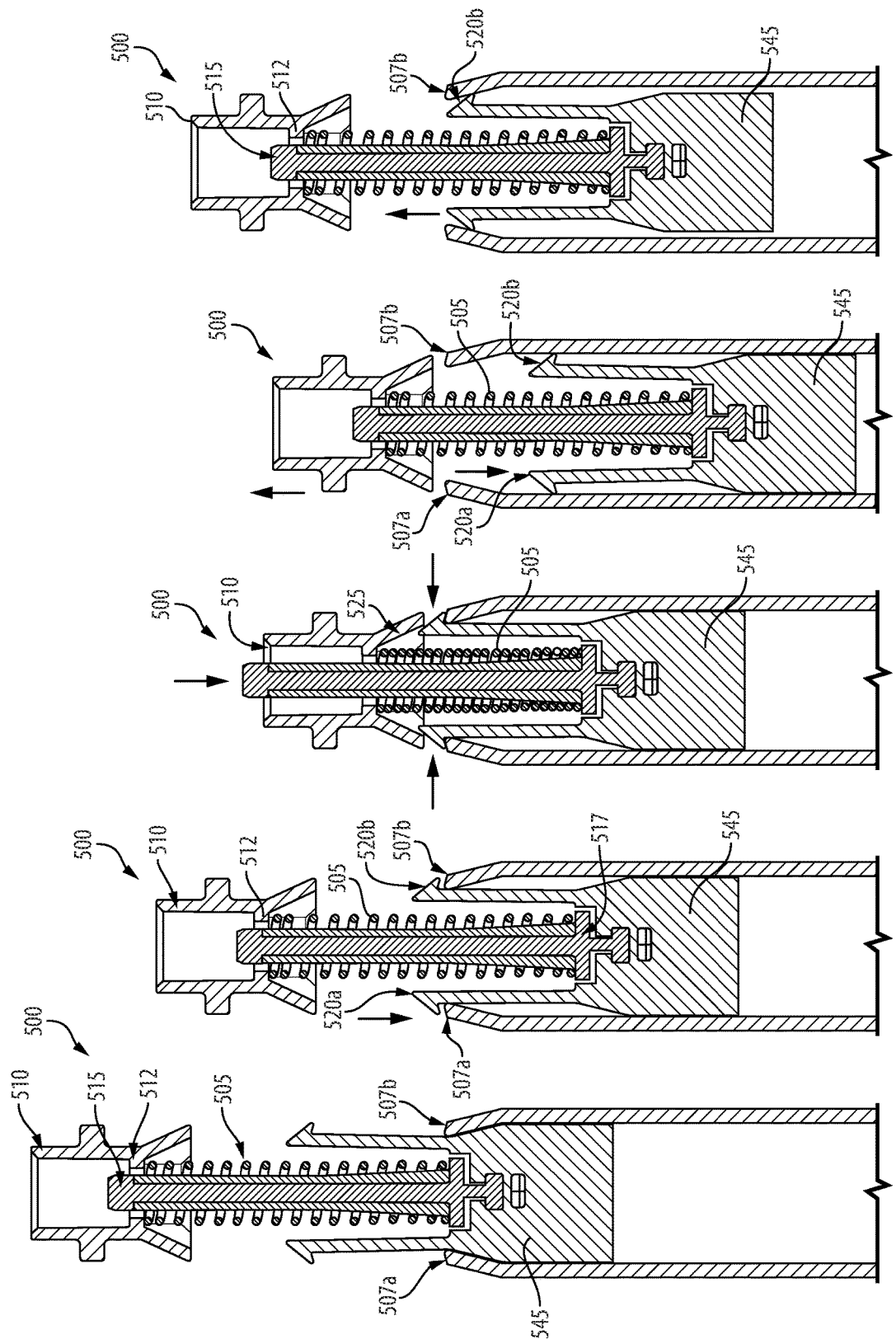

DEVICES FOR DEPLOYING TISSUE FASTENERS

CROSS-REFERENCE TO RELATED APPLICATIONS

This application claims priority to, and the benefit of, U.S. Provisional Application No. 63/318,967, filed Mar. 11, 2022, the content of which is incorporated by reference herein in its entirety.

FIELD OF THE INVENTION

The present invention generally relates to medical devices, and, more particularly, to medical devices that deploy bioabsorbable fasteners into tissue to secure two sides of an incision or wound in the skin of a patient.

BACKGROUND

There are many examples of surgical staplers which deliver staples into tissue to hold an incision or cut closed for healing. Most surgical staplers deliver traditional metal staples which rely on the strength of the staple to pierce the tissue and to hold the tissue surfaces together. One of the disadvantages of the metal staple is that it must have a portion that remains exposed through the skin surface in order to allow a medical professional to remove the fastener once biological healing is complete. This exposed portion is unsightly, and the puncture points, where the fastener enters the skin, have a risk of infection.

To address the disadvantages of metal staples, various inventors have proposed fasteners made of bioabsorbable materials which can be placed below the surface of the skin. This subcuticular skin closure avoids punctures through the epidermis and does not require follow-up removal of the staples. Such a solution is described, for example, in U.S. Pat. No. 6,726,705 issued to Peterson et al. ("Peterson") titled "Mechanical Method and Apparatus for Bilateral Tissue Fastening". The apparatus proposed by Peterson uses a driving head positioned in the incision at least partially below the exterior surface. Tissue manipulators compress the two sides of the tissue into concave areas of the driving head so that piercing members can cut holes in the target tissue zones to insert the fastener. After the fastener is deployed, the driving head is removed, thereby leaving the fastener bilaterally engaged in the tissue.

Fasteners embodying the Peterson invention are significantly thicker in cross section than a metal staple. This is necessary to enable the bioabsorbable fastener to be strong enough to maintain the traditional "U" shape of a staple during the healing process. This added bulk is undesirable and requires piercing members that can cut holes in the target tissue zones to insert the fastener. Such cutting of the tissue causes trauma and bleeding which can impact the healing process. Furthermore, staplers embodying the Peterson invention require that the driving head be partially inserted into the incision and the tissue compressed into concave areas of the driving head. For short incisions, such as those employed in minimally invasive surgery, devices based on Peterson are not suitable because the driving head can get trapped inside the incision once the fastener is deployed to hold the incision closed. Thus, staplers embodying the Peterson have drawbacks and limitations.

More recently, a hand-held stapler that deploys bioabsorbable fasteners without placing a driving head inside the incision is described in U.S. Pat. No. 8,506,591 issued to Danielson et al. ("Danielson") titled "Tissue Fasteners and Related Insertion Devices, Mechanisms, and Methods". In addition, Danielson teaches surgical needles extending through the legs of a fastener, with sharp tips exposed distally, which aid the fastener to enter the tissue with minimal cutting and bleeding. However, such an insertion mechanism has not gained acceptance by the surgical community, possibly because it requires two people to operate the device, which includes a first person to use forceps in each hand to evert the two sides of the incision, and a second person needed to operate the stapler.

SUMMARY

The present invention addresses the drawbacks of current staplers. In particular, the surgical device of the present invention is operable by a single user and able to deploy bioabsorbable fasteners, of the type described by Danielson, which are very small and have low mass to thereby minimize foreign material in the wound and further able to close incisions or wounds as short as 10 mm. Furthermore, in some embodiments, the device comprises surgical needles extending through the legs of the fastener, with sharp tips exposed distally, which aid the fastener to enter the tissue with minimal cutting, bleeding or trauma to the tissue when used to insert bioabsorbable fasteners for securing the two sides of an incision or wound.

In particular, the surgical device of the present invention is capable of everting and holding tissue from each side of an incision or wound and inserting one or more bioabsorbable fasteners into the subcuticular tissue to hold the two edges together. For example, the device comprises a housing which orients and constrains other elements of the device. The housing comprises a body with a handle element and a barrel element. The barrel of the housing has a proximal end and a distal end and an axis extending from the proximal end to the distal end through the center of the barrel. The barrel and handle elements are joined at an angle that facilitates the user holding the handle in one hand and positioning the barrel such that the axis is substantially perpendicular to the surface of the skin and directed toward the incision. The handle element includes a trigger extending from the housing where the barrel and handle are joined that may be moved toward the handle by a squeezing action of the user's hand and serves as an actuator for the moving elements of the device. The distal elements of the trigger are contained within the housing where the barrel and handle elements are joined.

The barrel element includes a fastener delivery mechanism containing a plurality of fasteners contained within a magazine. The magazine includes a cap to form an enclosure that contains the plurality of fasteners and other components such as a pusher, a pusher spring, a fastener support and a fastener support spring. The fastener delivery mechanism comprises mechanical elements such as a plunger needle assembly, timing lever, timing lever spring, and insertion device to release fasteners one-by-one when the trigger is operated by the user.

The distal end of the barrel element comprises an introducer with shaped features that aid the user in manipulating the tissue while holding the device in one hand and forceps in the other. The introducer includes a retraction finger which can engage one apex of an incision and can be pulled to create traction on tissue held at the other apex by forceps. When the tissue is placed in traction, the two edges of the incision become aligned and can be lifted above the plane of the skin surface. Once the tissue is raised to cover the introducer, movable tissue holders on each side of the barrel are operated by squeezing the trigger. The tissue holders each include a pincer to aid in securing the tissue. The user can alternately squeeze and release pressure on the trigger if the user desires to reposition the tissue. Once the user is satisfied with the position of the tissue, continued squeezing of the trigger moves the tissue holders such that the pincers secure both edges of the incision and the feet evert the tissue and position it for insertion of the fastener.

In order to place fasteners into short incisions, including incisions less than 10 mm long, the barrel and handle elements are joined at an angle that facilitates the user positioning the barrel substantially perpendicular to the surface of the skin and directed toward the incision. The introducer and tissue holders are configured such that short incisions can be secured and the fastener deployed completely distal to the tissue holding apparatus. This novel combination of inventive elements allows the user to deploy a fastener straight down into a short incision and then to simply lift the device from the site. This inventive configuration avoids the risk of the device becoming entrapped in the closed incision which has occurred in devices which comprise tissue holding elements that must be positioned inside the incision distal to the fastener.

When holding tissue only from the proximal side of the insertion forces there is a risk of the tissue stretching away from the holding components and not being pierced. The present invention teaches a shaped tip for the pincers that reduces stretch and secures the tissue with minimal trauma. The width of the pincer is 4-8 mm and comprises sharp protrusions on either side of the path of the fastener with a space between. The separation of the sharp protrusions reduces the stretch of the tissue compared to single point traditional forceps. The atraumatic holding of the tissue is also facilitated by the pincer arm which allows movement in multiple dimensions. Movement of the pincer arm working in conjunction with the surface of the introducer against which the tissue is pinched (referred to as pinch rails), has the effect of increasing the engagement of the pincers on the tissue as the fastener penetration forces try to pull the tissue away. The result is less stretch of the tissue and adaptive holding forces with less force per unit area than competitive tissue manipulators.

In the present invention, the sequential steps of pinching the tissue and deploying the fastener are both controlled by squeezing a single trigger. To accomplish this the present invention comprises a novel interrupted motion slider-crank assembly to transfer force from the trigger to the tissue holders and the insertion device. During the initial movement, a slider-crank mechanism similar to those known in the art, transfers force from the trigger to the tissue holders. During the second phase the downward force on the proximal end of the slider is transferred to a lateral force that moves the proximal end of the slider along an angled surface. This movement creates downward force on the slider with significant distal force from the mechanical advantage of the two mating angled surfaces (ramps). This mechanical advantage allows the user, who is squeezing the trigger, to strongly secure the tissue between the pincer and the introducer. During the third phase, the movement of the slider is "interrupted" by transitioning the proximal end of the slider to a latch so that the slider and tissue holders stop moving and continued squeezing of the handle by the user operates on the insertion device to deliver the fastener to the tissue.

In one embodiment of the present invention, a ratchet mechanism can be included that allows the user to re-open the pincers to reposition on the tissue, but then requires the user to complete the fastener placement before allowing the trigger to return to its starting position. The ratchet mechanism is preferably designed to be overcome by the user in case the mechanism jams. Types of ratchets include spring loaded pawl on saw teeth, flexible metal sheet sliding over cam or saw teeth, or other ratchet mechanisms known to those skilled in the art.

In an alternate embodiment of the present invention, the risk of tissue stretch is mitigated by increasing the velocity of the insertion mechanism. A velocity of about 6-7 m/s and a kinetic energy of about 0.15-0.2 N-m gives good penetrations with minimal stretch. Needle insertion products such as insulin pumps and auto-injection delivery devices are known in the prior art. These devices require separate actions to pre-load a spring and then to trigger/fire the device. Other mechanisms such as those described in U.S. Pat. No. 10,918,381 directly impact the fastener with the high velocity driver. In order to deploy a bioabsorbable fastener of the type described by Danielson, each fastener must be installed on the insertion needles in a first step. Attempting to install the fastener on needles at a high velocity has the risk of jamming the mechanism. Therefore, the first step must occur at a modest velocity prior to acting on the insertion device with a high velocity delivery system. To achieve this, this alternate embodiment comprises a multi-velocity spring-loaded delivery mechanism.

At the beginning of deploying a fastener, a driving head is advanced at a modest speed, moved by the user squeezing the trigger. The driving head acts on a plunger needle assembly indirectly through a compression spring. As the plunger needle assembly moves distally, it inserts needles into the front-most fastener in the stack of fasteners. A sear—stop mechanism halts movement of the plunger needle assembly once the fastener is installed on the needles. Continued squeezing of the trigger causes the spring to be compressed, storing energy to use in inserting the fastener. A release element releases the spring to deliver its stored energy to the insertion device propelling the fastener rapidly to contact the dermal tissue at a velocity in excess of 6 m/s. After insertion the user releases the trigger, and the driving head is pulled upwards thus returning all elements to their starting positions.

Accordingly, the device of the present invention can be operated by a single user so as to aid in the insertion of one or more bioabsorbable fasteners of the type described by Danielson for closing incisions and wounds (including small incisions such as ones that are less than 10 mm long). For example, the device includes a shaped distal member configured to engage one apex of an incision to provide traction to oppose forces from forceps applied at the other apex and operated by the user's other hand, thereby providing an improved means of achieving the end goal of closing incisions or wounds without needing the assistance of another person. The device further includes tissue pinching and folding members operably controlled by the user during actuation of a trigger of the device, which can temporarily secure and expose inner surfaces of two edges of an incision or wound, where one of a plurality of fasteners can be inserted upon further actuation of the trigger, without crushing or causing undue trauma to the tissue and further aids a single user in accurately deploying fasteners to the intended target.

In one aspect, the inventions provides a hand-held surgical device for deploying bioabsorbable fasteners to close a wound or incision in tissue. The device includes a body comprising a handle element including a user-actuatable trigger and a barrel element including a distal end for positioning one or more fasteners relative to a wound or incision in tissue. The device further includes a tissue pinching and folding assembly positioned adjacent to the distal end of the barrel element and operably coupled to the trigger, wherein, upon placement of the distal end of the barrel element relative to a wound or incision and in response to user actuation of said trigger, the tissue pinching and folding assembly is configured to temporarily secure and physically evert opposing edges of the wound or incision relative to the distal end of the barrel element in preparation for deployment of one or more of a plurality of fasteners. The device further includes a fastener delivery mechanism operably coupled to the trigger and configured to deploy one or more of a plurality of bioabsorbable fasteners from the distal end of the barrel element in response to user actuation of said trigger.

In some embodiments, the fastener delivery mechanism is configured to cause a given fastener to extend outwardly and away from a distal-most end of the tissue pinching and folding assembly and the distal-most end of the barrel and subsequently penetrate opposing edges of the wound or incision such that the fastener is deployed entirely distal to the device and delivered below the surface of the tissue.

The tissue pinching and folding assembly may generally include: 1) an introducer positioned at, and extending from, the distal end of the barrel element, the introducer comprising an elongate body configured to directly contact opposing edges of the wound or incision; and 2) a pair of opposing tissue holder elements positioned at the distal end of the barrel element and on opposing sides of the elongate body of the introducer, each tissue holder comprising a pincer member and a foot member configured to cooperatively move with one another relative to the introducer in response to user actuation of the trigger.

The elongate body of the introducer may include a pair of pinch rails extending along the opposing sides of the elongate body. Each tissue holder element may include a pincer element and a foot element, wherein, in response to user actuation of the trigger, the pincer element is adapted to pinch and secure a portion of a corresponding edge of the wound or incision against a corresponding pinch rail and the foot element is adapted to evert a portion of the corresponding edge of the wound or incision to thereby position an inner surface thereof for subsequent receipt of a portion of a fastener. For example, each pincer may include one or more sharp protrusions.

The introducer may include an exit through which at least a fastener passes during operation of the fastener delivery system in response to user actuation of the trigger. The foot element of each tissue holder element is generally adapted to expose the inner surface of the respective edge of the wound or incision relative to the exit of the introducer such that a deployed fastener passing through the exit is able to bilaterally engage the opposing edges of the wound or incision and thereby hold said edges together.

The trigger is operably coupled to the pair of tissue holder elements and the fastener delivery mechanism by way of independent connections allowing for sequential operation thereof.

As such, user actuation of the trigger to an initial first position may cause the pincer member of each tissue holder element to rotate inwardly toward the introducer and further pinch and secure a portion of a corresponding edge of the wound or incision against a corresponding side of the introducer. Furthermore, user actuation of the trigger to a subsequent second position may cause the foot member of each tissue holder element to rotate inwardly toward the introducer and further evert a portion of the corresponding edge of the wound or incision to thereby position an inner surface thereof for subsequent receipt of a portion of a fastener. Finally, user actuation of the trigger to a subsequent third position may cause operation of the fastener delivery mechanism resulting in deployment of a fastener to bilaterally engage the opposing edges of the wound or incision and thereby hold said edges together.

In some embodiments, each tissue holder element may be injection molded from a single material. For example, in some embodiments, the pincer member and foot member of each tissue holder element are monolithically formed with one another.

In some embodiments, the pincer member and foot member of each tissue holder element may be formed from different materials and assembled to cooperatively form a given tissue holder element.

The pincer member and foot member may generally be movable relative to one another.

In some embodiments, the device further includes a pair of slider elements, each slider element having a proximal end operably coupled to the trigger and a distal end operably coupled to a respective one of the pair of tissue holder elements such that actuation of the trigger causes movement of the pair of slider elements which, in turn, causes corresponding movement of the pair of opposing tissue holder elements.

In some embodiments, the introducer may further include a retraction finger positioned at one end of the elongate body and adapted to engage a first apex of the wound or incision to thereby provide traction opposing forces applied at a second apex of the wound or incision.

The fastener delivery mechanism may generally be configured to retain a plurality of fasteners and further comprises one or more insertion needles configured to releasably engage and deploy each of the plurality of fasteners in a one-by-one fashion in response to repeated user actuations of the trigger.

It should be noted that, in some embodiments, each of the plurality of fasteners includes a first leg, a second leg, and a flexible bridge member connecting the first and second legs. In some embodiments, each leg may be fully cannulated such that respective insertion needles of the fastener delivery mechanism, which are configured to releasably engage and deploy each of the plurality of fasteners, can pass through each respective leg such that a sharp end of the insertion needle is exposed distally. For example, the trigger may be operably coupled to a plunger-needle assembly, the plunger-needle assembly comprising two insertion needles parallel to each other and configured to pass through a respective leg of a fastener. As such, in response to user actuation of the trigger, the plunger-needle assembly may cause the insertion needles to engage a fastener and simultaneously penetrate opposing edges of the wound or incision thereby inserting the fastener and, in response to user releasing the trigger, the plunger-needle assembly causes the insertion needles to leave the fastener completely distal to the device and below the tissue surface.

In other embodiments, each leg may be partially cannulated, in that a passageway within each leg does not entirely extend through each leg but rather extends only partially within each leg. Accordingly, in such an embodiment, respective insertion needles of the fastener delivery mechanism pass within a portion of a respective partially-cannulated leg of a fastener and a sharp end is not distally exposed, but remains within the passageway of a respective leg. For example, the trigger may be operably coupled to a plunger-needle assembly, the plunger-needle assembly comprising two insertion needles parallel to each other and configured to pass within a portion of a respective partially-cannulated leg of a fastener, and, in response to user actuation of the trigger, the plunger-needle assembly causes the insertion needles to engage a fastener and thereby cause each leg of the fastener to penetrate opposing edges of the wound or incision thereby inserting the fastener and, in response to user releasing the trigger, the plunger-needle assembly causes the insertion needles to leave the fastener completely distal to the device and below the tissue surface.

The fastener delivery mechanism may generally be configured to receive and retain a magazine comprising a plurality of stacked fasteners and the plunger-needle assembly is configured to releasably engage, by way of the pair of insertion needles, the front-most fastener arranged in the stack of fasteners for subsequent deployment.

In some embodiments, the fastener delivery mechanism may include a spring-powered delivery assembly. The spring-powered delivery assembly may include: a plunger-needle assembly configured to releasably engage a forward-most fastener in a stack of fasteners provided in a magazine; a driving head operatively coupled to the trigger and the plunger-needle assembly, wherein the driving head is configured to move the plunger-needle assembly indirectly through actions on a driving spring; a stop-mechanism comprising sears configured to engage corresponding stops and thereby arrest movement of the plunger-needle assembly when the driving head is moved to a first driving head position; and a release element adapted to disengage the sears from the corresponding stops when the driving head is moved to a second driving head position.

Accordingly, in such an embodiment, user actuation of the trigger to an initial first position causes the driving head to move to the first driving head position and the plunger-needle assembly to engage the forward-most fastener. Then, user actuation of the trigger to a subsequent second position causes the driving spring to compress and the driving head to move to the second driving head position such that, upon disengagement of the sears from the corresponding stops, the plunger-needle assembly is driven via force imparted from the compressed driving spring to thereby deploy and deliver the fastener into tissue at a speed substantially faster than movement of the trigger

BRIEF DESCRIPTION OF THE DRAWINGS

In the drawings, like reference characters generally refer to the same parts throughout the different views. When components are symmetrical, the numbered features will be labeled with "a" for the left side and "b" for the right side, but in the text these symmetrical elements will be identified as "a,b", even if only one component is visible in a particular drawing. Also, the drawings are not necessarily to scale, emphasis instead generally being placed upon illustrating the principles of the invention.

FIGS. 12A, 12B, 12C, 12D, and 12E shows embodiments of the additional components highlighted from FIG. 11 in a series of steps to illustrate the movement of the components as the trigger is squeezed by the user.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present invention is directed to medical devices that deploy fasteners into tissue to secure two sides of an incision or wound in the skin of a patient. In particular, the present invention provides a hand-held surgical device, operable by a single user, for delivering fasteners for closing wounds or incisions. The device provides tissue pinching and folding members integrated in the device and controlled by the user which can temporarily secure and expose the inner surfaces of the two edges of an incision or wound where the fastener is to be inserted without crushing or causing undue trauma to the tissue.

It should be noted that the device of the present disclosure is configured to deploy and insert fasteners of the type having two cannulated legs into tissue using a similar tissue insertion procedure/steps as set forth in Danielson, but further includes novel and innovative delivery mechanisms for providing numerous advantages and addresses the drawbacks of current stapler devices similar to Peterson and Danielson. It should be further noted that other types of bioabsorbable fasteners may also be used with and deployed by the disclosed device. The present invention further includes certain mechanical elements for deploying a given fastener similar to those mechanical elements described in commonly assigned U.S. Pat. No. 9,232,943, issued to Rogers and Milea ("Rogers") titled "Delivering Bioabsorbable Fasteners", the content of which is incorporated by reference herein its entirety.

Figure 1:
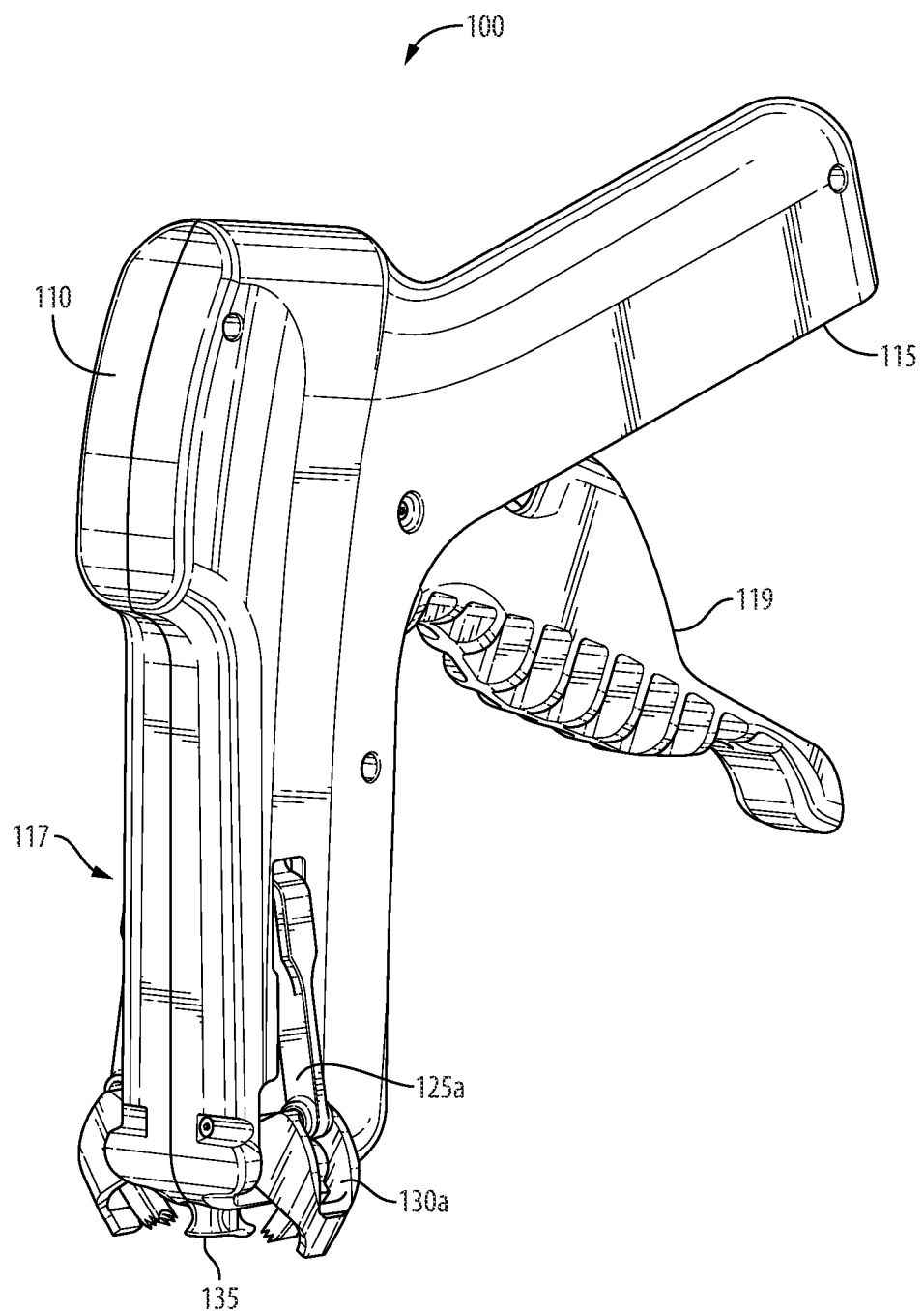
FIG. 1 shows a perspective view of an embodiment of the assembled apparatus of the present invention.

FIG. 1 illustrates a perspective view of an embodiment of the device 100 for inserting bioabsorbable fasteners to secure the two sides of an incision in tissue. The device comprises a housing 110 with a handle 115 and a barrel 117 joined at an angle. Extending from the housing is a trigger 119 that may be moved toward the handle 115 by a squeezing action of the user's hand and serves as an actuator for the moving elements of the device.

The barrel of the housing has a proximal end and a distal end and an axis extending from the proximal end to the distal end through the center of the barrel. For purposes of this description, the proximal end is at the top left of the figure and the distal end, the end farthest from the user, is at the bottom left of the figure. The barrel and handle elements are joined at an angle that facilitates the user holding the handle in one hand and positioning the barrel 117 such that the axis is substantially perpendicular to the surface of the skin and directed toward the incision. The user operates the device by manually squeezing the trigger 119 such that the trigger is pulled back towards the handle.

The trigger is operatively connected to sliders 125a, 125b on each side of the barrel 117. The tissue holder 130a, 130b, which is described in detail below, includes tissue holder pivot pins which allow the tissue holder to be rotatably attached to the housing 110 by locating the pins into recesses in the housing shell. The tissue holder 130a, 130b also comprises a tissue holder push bar which can be rotatably connected to the distal end of the slider 125a, 125b. Movement of the sliders transfers force from the trigger 119 to the tissue holders 130a, 130b. At the distal end of the barrel the device includes an introducer element 135 generally in the form of a protrusion. The introducer 135 acts in conjunction with the tissue holders 130a, 130b to position and hold the tissue for insertion of the fasteners.

Figure 2:
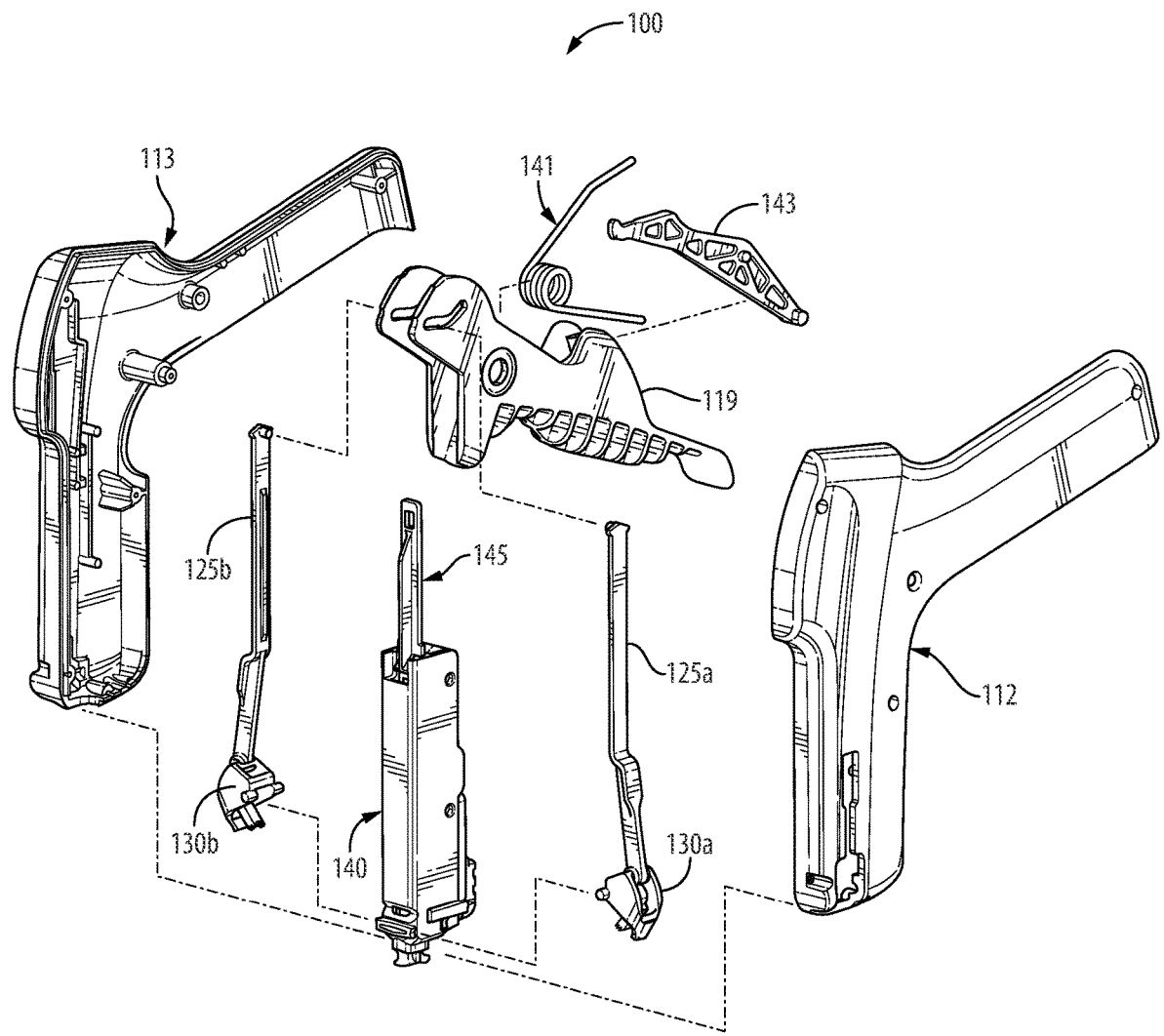
FIG. 2 is a partially exploded perspective view of the embodiment of FIG. 1 of the present invention showing the major sub-assemblies.

FIG. 2 shows the major sub-assemblies of the embodiment of FIG. 1 of the present invention in an exploded view. The device 100 comprises a left housing shell 112 and a right housing shell 113 which are assembled together to form the housing which orients and constrains other elements of the device.

The device includes a fastener delivery mechanism 140 containing a plurality of fasteners contained within a magazine. As described in detail below, the fastener delivery mechanism comprises mechanical elements to release fasteners one-by-one when the trigger 119 is operated by the user. In some embodiments, the mechanical elements of the fastener delivery mechanism are similar to those elements described in Rogers and essentially interact with the fasteners in a similar manner. The plunger-lever 143 transfers force from the trigger 119 to the plunger-needle assembly 145 of the fastener delivery mechanism 140. A spring 141 provides restorative force to return the trigger to its starting position when squeezing pressure is released.

As described in detail below, the tissue holder 130a, 130b also comprises a tissue holder push bar which can be rotatably connected to the distal end of a slider 125a, 125b.

Figure 3:
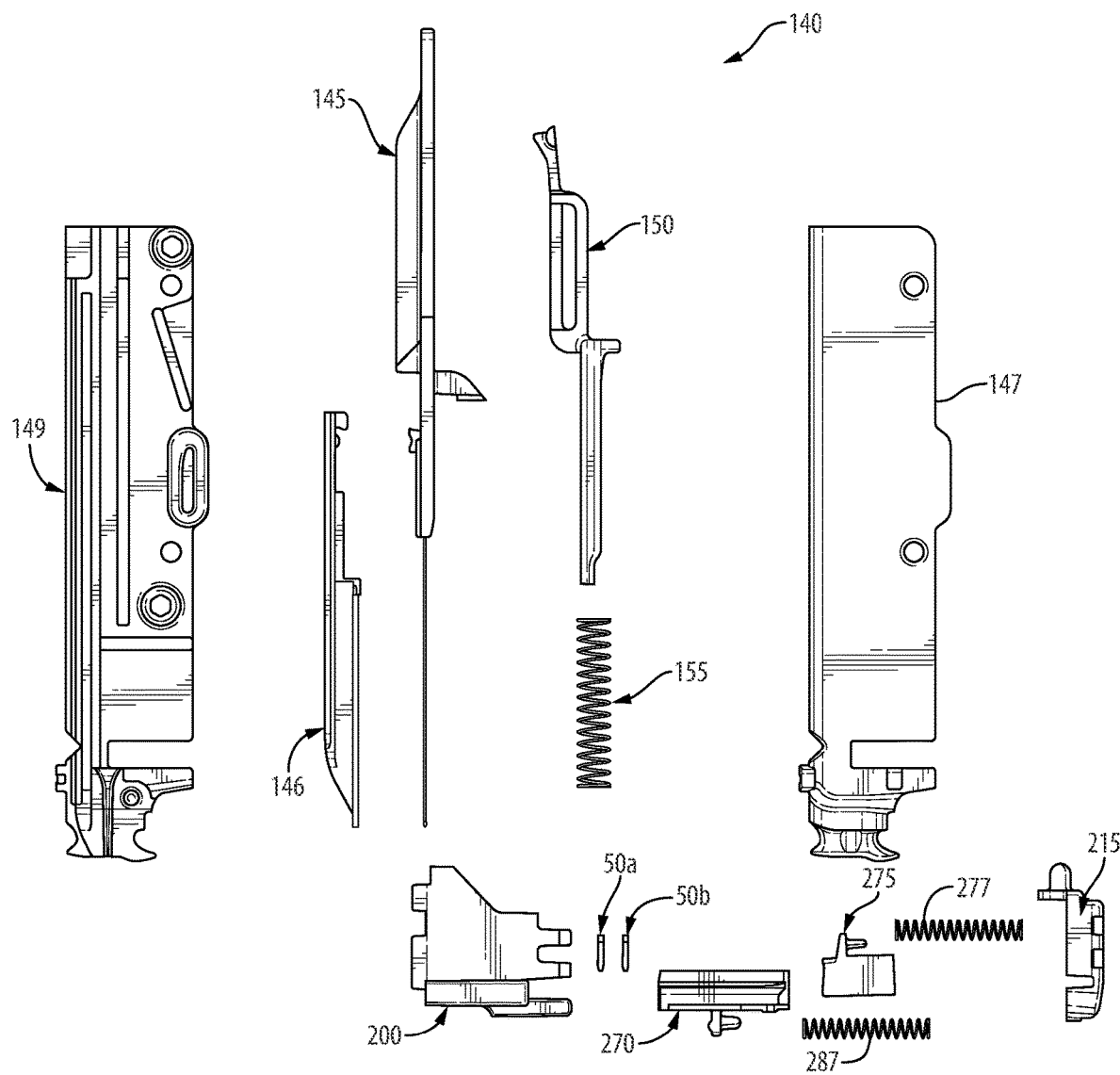
FIG. 3 shows the elements of an embodiment of the fastener delivery mechanism of FIG. 2 in an exploded view.

FIG. 3 shows the elements of an embodiment of the fastener delivery mechanism 140 of FIG. 2 in an exploded view. The components of the fastener delivery mechanism are contained within two shells, the delivery mechanism left housing 147 and the delivery mechanism right housing 149. When the two housings are assembled, they guide the plunger needle assembly 145 to enable it to move in response to the plunger lever 143 (not shown) and to cooperate with the other components of the assembly to deliver fasteners one at a time. The components shown in FIG. 3 with like reference characters to the same parts in FIGS. 3, 4, and 5 of Rogers and generally have the same form, fit and function as described in Rogers. The plunger 40 with needles 65 described by Rogers is replaced by the plunger needle assembly 145 in the present invention, and modified to replace the manually driven thumb pad with a connection to the plunger lever 143. The guide tube support 73, and needle guide tubes 67 described in Rogers is renamed as insertion device 146 but maintains the same function.

As detailed in Rogers, the fastener delivery system 140 includes a magazine cap 215 which assembles together with magazine 200 to form an enclosure that contains a plurality of fasteners. The fasteners are positioned on a reciprocally movable fastener support 270 which is connected to a pusher 275, pusher spring 277, and fastener support spring 287 to advance the fasteners illustrated as a first fastener 50a and a second fastener 50b. Needle guide tubes and the legs of the front-most fastener are in slidable contact with at least one alignment surface configured to axially align them. Two needles within the needle guide tubes are actuated to insert each needle into a cannulated leg. A timing lever 150 connected to a lever support spring 155 acts on the fastener support 270 in concert with the actuator movement to remove support of the forward-most (also referred to herein as the "front-most") fastener after the needles are inserted. The needle guide tubes transfer force to the fastener to push it out of the magazine to insert it into the tissue.

The fasteners may be a type such as is described in Danielson wherein the fastener includes a bridge section and two cannulated leg sections. The bridge section includes a first portion and a second portion. The first leg section is integral with the bridge section and extends from the first portion of the bridge section. At least a portion of the first leg section defines a first lumen extending therethrough such that the first leg section is cannulated. The second leg section also is integral with the bridge section, and it extends from the second portion of the bridge section. At least a portion of the second leg section defines a second lumen extending therethrough such that the second leg section also is cannulated. The bridge section and the first and second leg sections comprise a single piece of material.

Figure 4:
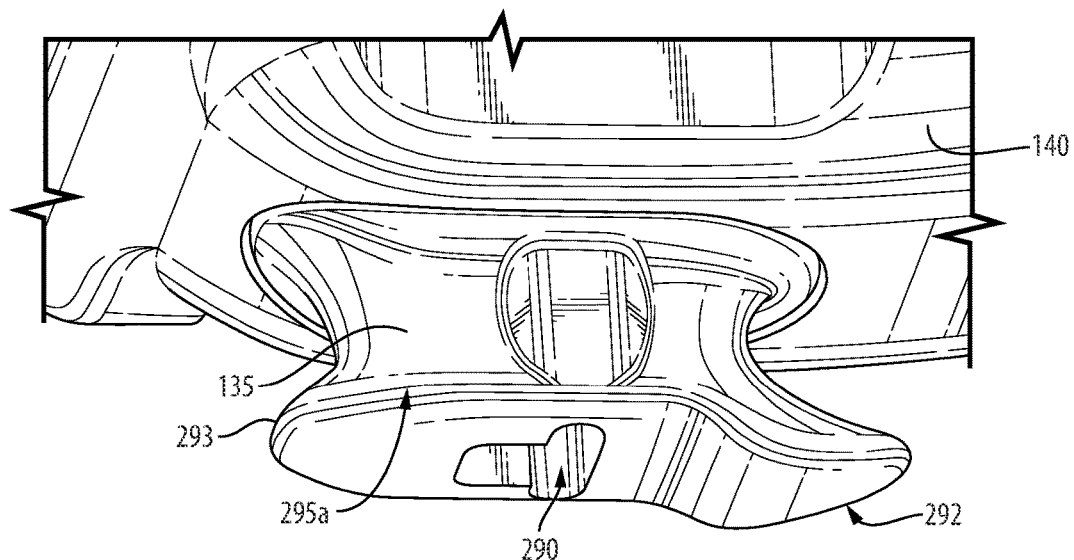
FIG. 4 is a close-up view of an embodiment of the introducer.

FIG. 4 shows the features of an embodiment of the introducer 135 which is located at the distal end of the fastener delivery mechanism 140. The introducer includes the exit 290, which is a specially shaped opening that guides the distal end of the plunger-needle assembly 145 as it exits the fastener delivery mechanism 140 carrying a fastener. The introducer 135 also has features that aid in manipulating and positioning the tissue. The elongated body of the introducer includes the retractor 292, or retraction finger, at one end and a point 293 at the opposite end. The retractor can engage one apex of an incision and be pulled by force exerted by the user in positioning the device to create traction on tissue held at the other apex by forceps. When the tissue is placed in traction, the two edges of the incision become aligned and can be lifted above the plane of the skin surface. When in use, the longer dimension of the introducer 135 is aligned with the incision. Along each side of the introducer 135, extending from the point 293 to the retractor 292, are pinch-rails 295a, 295b. As described in detail below, when the two sides of the incision are lifted, the inner surfaces of the tissue contact the introducer 135 and fold around the pinch-rails to hold the tissue in place.

Figure 5:
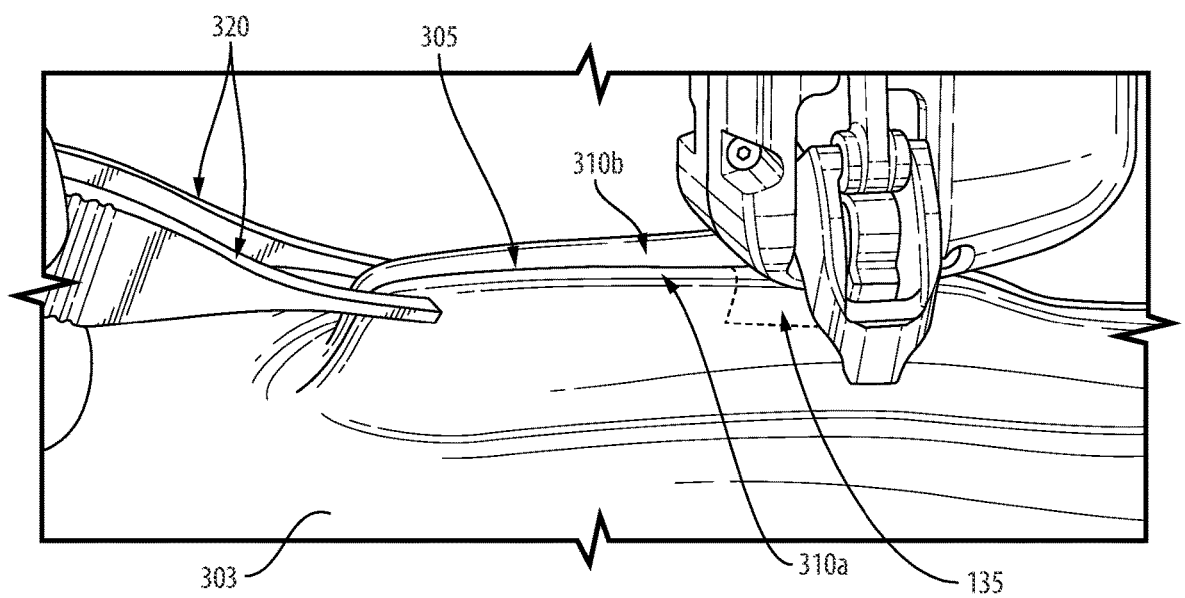
FIG. 5 shows a typical incision in skin with an embodiment of the present invention positioned for closing.

FIG. 5 shows one embodiment of the present invention in contact with an opening 305 in skin tissue 303 as may be representative of the present invention in use. The introducer 135 is covered by the raised tissue with the retractor 292 (not visible) engaged at the apex of the incision on the right of the figure, and forceps 320 pulling at the other apex to create traction on tissue edges 310*a*, 310*b*. When the tissue is placed in traction, the two edges 310*a*, 310*b* of the opening or incision become aligned and can be lifted above the plane of the skin tissue 303 surface. When the two sides of the incision are lifted as shown in FIG. 5, the inner surfaces of the tissue contact the introducer 135 and fold around the pinch-rails 295*a*, 295*b* (not visible).

Figure 6:
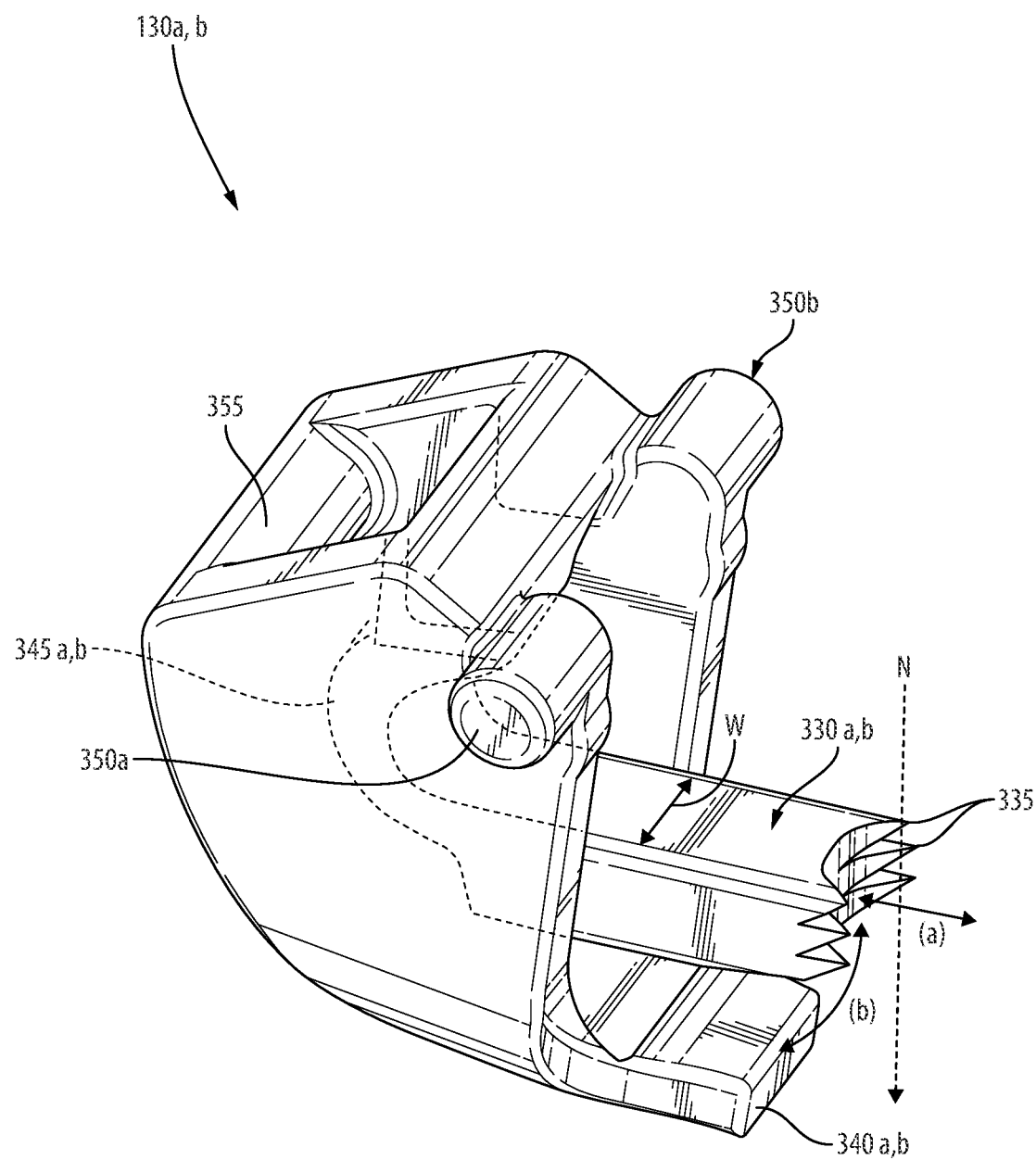
FIG. 6 is a perspective view of an embodiment of one of the tissue holders of the apparatus of FIG. 1.

FIG. 6 shows an embodiment of one of the tissue holders 130*a*, 130*b*, displaced from its movable attachment to the side of the barrel 117 for purposes of this description. Each tissue holder includes tissue holder pivot pins 350*a*, 350*b* which allow the tissue holder to be rotatably attached to the housing 110 by locating the pins into recesses in the housing shell. Each tissue holder 130*a*, 130*b* also comprises a tissue holder push bar 355 which can be rotatably connected to the distal end of a slider 125*a*, 125*b*. Each tissue holder 130*a*, 130*b* further comprises a pincer 330*a*, 330*b* and a foot 340*a*, 340*b*.

Each pincer 330*a*, 330*b* includes sharp protrusions or teeth 335 at the distal end which are generally directed toward the introducer (not shown). Two rows of teeth 335 are advantageously positioned on the distal end of the pincer with a space between. The space between the teeth 335, which is aligned with the path (N) of the fastener, has the effect of increasing the engagement of the teeth as the fastener penetration forces pull in the area between the teeth. The width (W) of the pincer exceeds 2 mm and preferably is between 4 mm and 8 mm. The width (W) combined with the separated teeth reduces the stretch of the tissue compared to single point traditional forceps. The pincer 330*a*, 330*b* is positioned at the end of a pincer arm 345*a*, 345*b* which is attached to the tissue holder 130*a*, 130*b* in such a way that the pincer can move relative to the tissue holder. One direction of movement (a) allows the pincer 330*a*, 330*b* to move toward and away-from the introducer 135*a*, 135*b*. Another direction of movement (b) allows the pincer 330*a*, 330*b* to move toward and away-from the foot 340*a*, 340*b*. The two movements combine to capture the tissue as illustrated in FIGS. 7A and 7B.

Figure 7A:
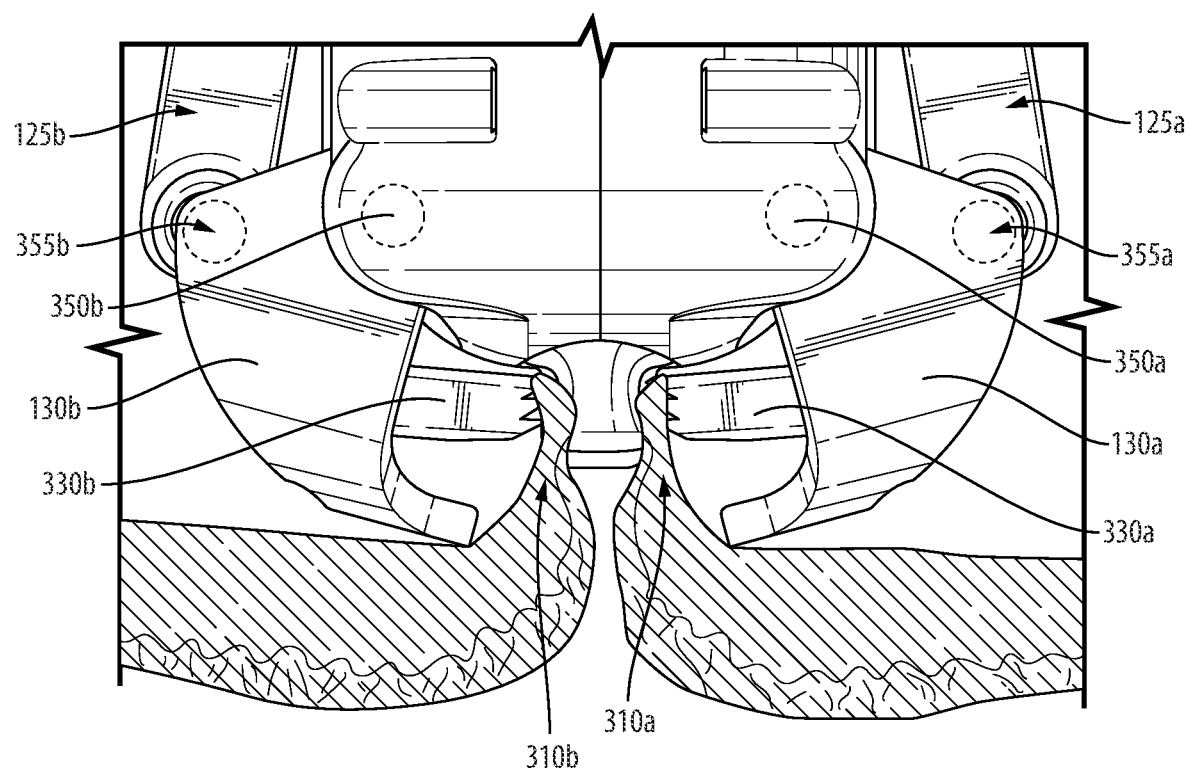
FIG. 7A is a front view of the distal end of the barrel of the apparatus of FIG. 1 and partial cross section of tissue showing the position of the tissue holders when the user squeezes the trigger to a first position.

FIG. 7A is a front view of the distal end of an embodiment of the barrel and partial cross sections of tissue showing the position of the tissue holders when engaging two tissue edges 310*a*, 310*b* of an opening in skin tissue. In this figure the tissue edges 310*a*, 310*b* have been raised by the user as shown in FIG. 5 wherein the introducer is covered by the raised tissue with the retractor engaged at one apex of the incision (not shown) and forceps pulling at the other apex (not shown) to create traction on tissue edges 310*a*, 310*b*. The user squeezes the trigger to a first position which moves the sliders 125*a*, 125*b* distally. As the sliders move, the distal end of each slider pushes against a tissue holder push bar 355*a*, 355*b* causing the tissue holder to rotate about the tissue holder pivot pins 350*a*, 350*b*. The rotation of the tissue holders 130*a*, 130*b* delivers force to the pincers 330*a*, 330*b* to engage the tissue as shown. During the initial squeezing of the trigger, the user can release and reapply pressure to reposition the tissue as further described in relation to FIG. 9A. Once the user is satisfied with the position of the tissue, continued squeezing of the trigger moves the tissue holders to the position shown in FIG. 7B.

Figure 7B:
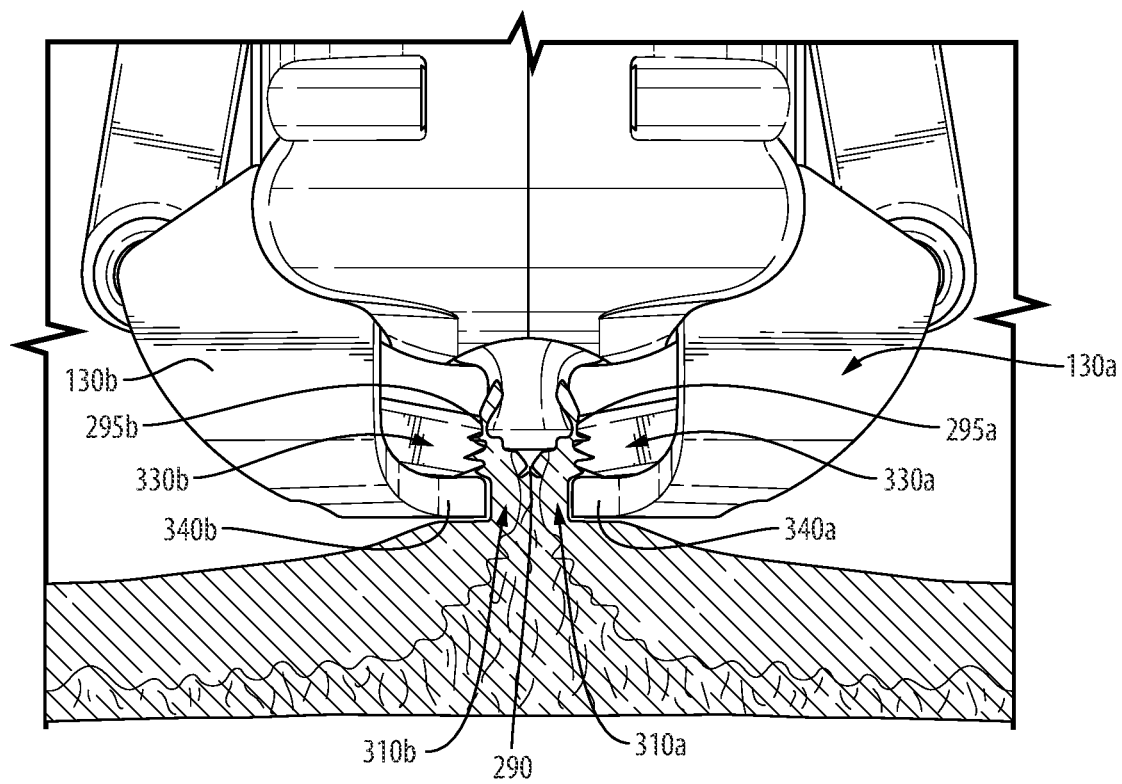
FIG. 7B shows an embodiment of the front view of the device and tissue of FIG. 7A after the user squeezes the trigger to a second position.

FIG. 7B shows the front view of the device and tissue of FIG. 7A after the user squeezes the trigger to a second position. In this position, the tissue holders 130*a*, 130*b* are rotated to a final position such that the feet 340*a*, 340*b* contact the tissue to move the tissue edges 310*a*, 310*b* of the opening directly in line with the fastener path distal to the exit 290 of the introducer. In this position, the tissue is trapped in a tortuous path around the pincers 330*a*, 330*b*, the pinch-rails 295*a*, 295*b* and the feet 340*a*, 340*b*. This tortuous path allows non-traumatic pressure to hold the tissue with sufficient traction for the fastener to pierce it. The unique action of the pincer (ability to move in direction "b" as indicated in FIG. 6) increases the pincer's ability to hold the tissue as the tissue is pulled distally by the insertion forces of the fastener.

Figure 7C:
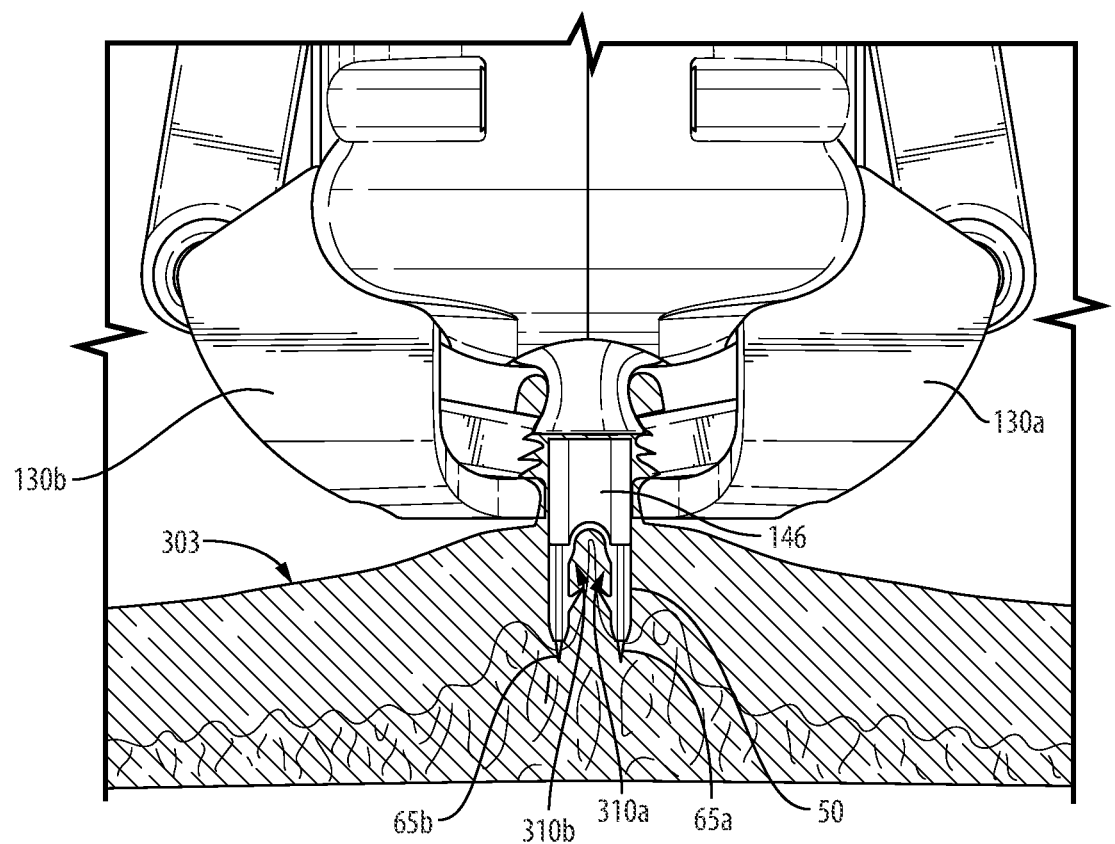
FIG. 7C shows an embodiment of the front view of the device and tissue of FIG. 7B after the user squeezes the trigger to a third position showing a cross section of the fastener and tissue after deployment of the fastener into the tissue.

FIG. 7C shows the front view of the device shown in FIG. 7B after the user squeezes the trigger to a third position. In this position, the forces applied distally by the plunger-needle assembly are applied to the insertion device 146 to fully deploy the fastener 50 into the two tissue edges 310*a*, 310*b* of the opening. Immediately after the deployment of the fastener, the user releases pressure on the trigger and the needles 65*a*, 65*b* retract within the insertion device 146 leaving the fastener 50 engaged in the tissue. At this point the fastener 50 is completely distal to all parts of the device allowing the user to fully release the tissue holders 130*a*, 130*b* and lift the device from contact with the skin tissue 303 without risk of being trapped in the opening.

Figure 8:
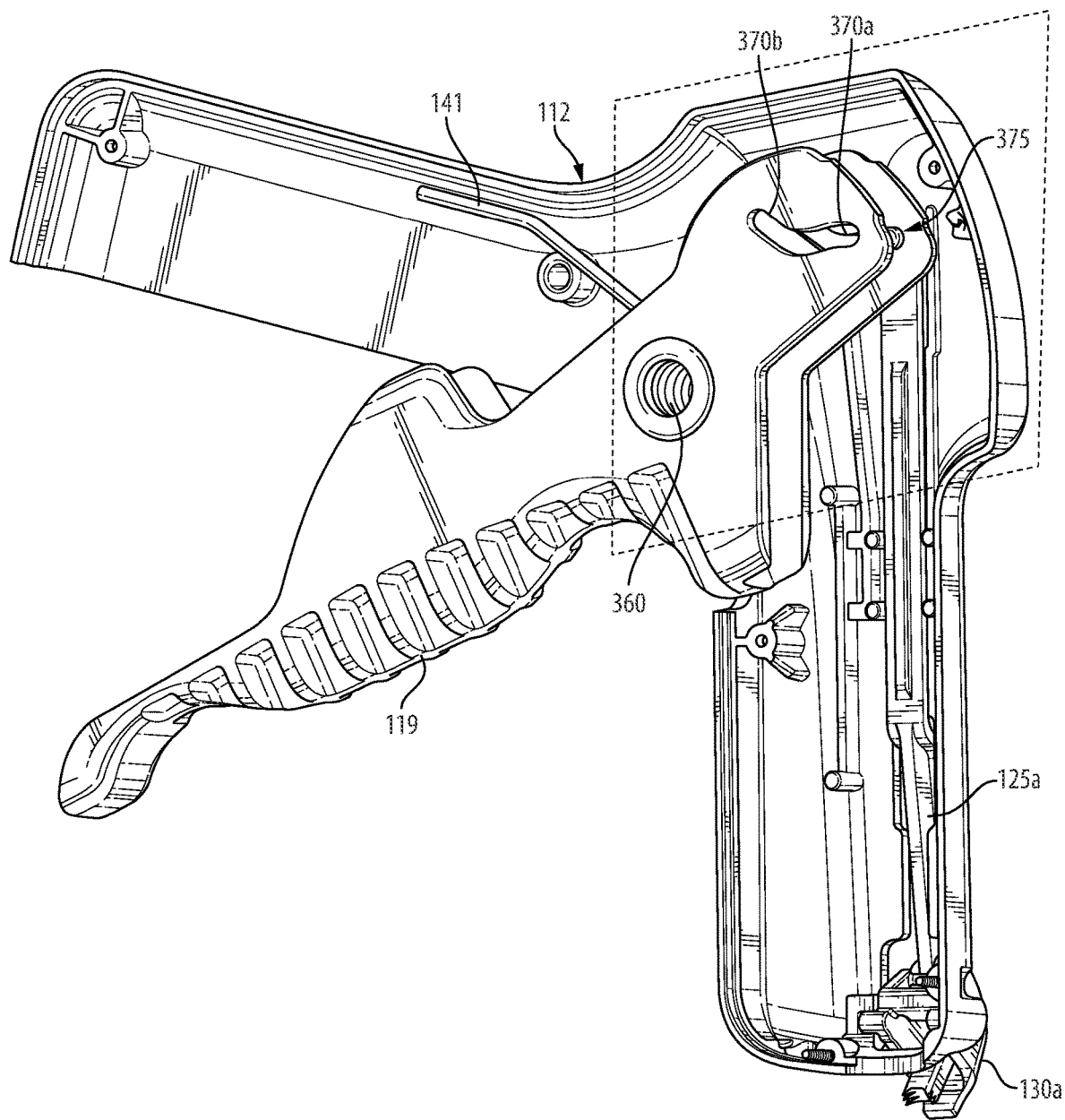
FIG. 8 shows an embodiment of the left housing shell of the apparatus of FIG. 1 assembled with selected components.

FIG. 8 shows an embodiment of the left housing shell 112 of the device of FIG. 1 assembled with only four (4) components: the trigger 119; the spring 141; a slider 125*a*; and a tissue holder 130*a*. The other components of the device are removed for purposes of this description. The trigger 119 rotates about trigger pivot hole 360 in response to the user squeezing the trigger. The trigger includes a bifurcated distal end within the housing with each distal element having a curved cam track 370*a*, 370*b*. Each cam track acts on a slider pin 375 to transfer force from the trigger to the slider. The dotted lines on FIG. 8 indicate a portion of the device that is further described in FIGS. 9A-9C.

Figure 9A:
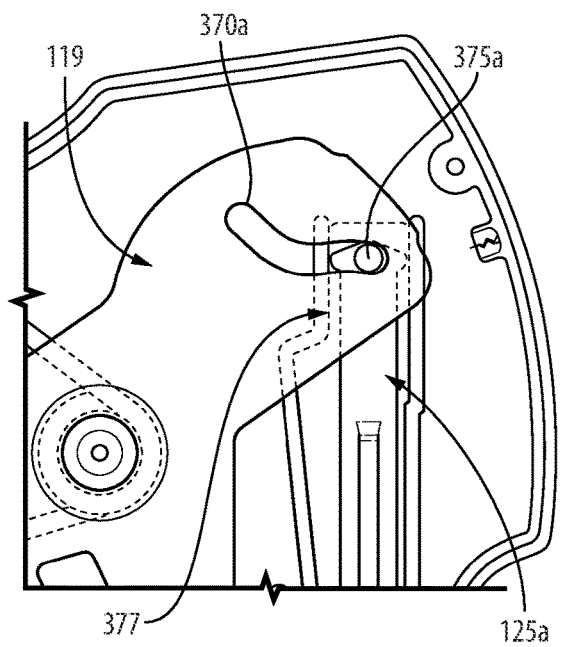
FIGS. 9A, 9B, 9C, and 9D show views of a portion of the apparatus outlined in FIG. 8 with a partial cross section of the trigger to illustrate movements of the components when the trigger is squeezed by the user.

FIG. 9A shows a close up view of a portion of an embodiment of the device in its initial position prior to operation by the user. The trigger 119 is shown in partial cross section to view only components on the left side of the device but the reader will appreciate that similar actions and configurations of components occur for elements on the right side of the device. In this figure, the distal element of the trigger 119 is shown with its curved cam track 370*a*. Cam track 370*a* engages slider pin 375*a* at the proximal end of slider 125*a*. In response to the user squeezing the trigger, the distal element comprising the cam track 370*a* acts on slider pin 375*a* to move the slider distally along slider track 377.

Figure 9B:
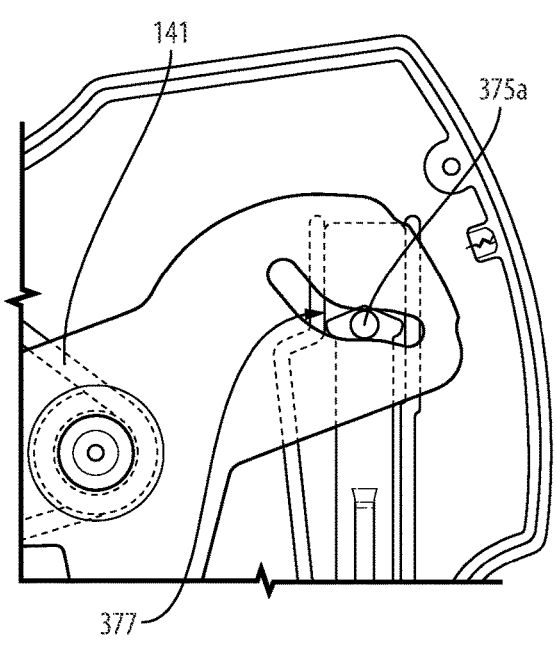

FIG. 9B shows the device of FIG. 9A after the trigger has been moved to a first position. At this first position, if the user releases pressure on the trigger the spring 141 reverses the rotation of the trigger and the cam track pulls the slider pin 375*a* towards its initial position as shown in FIG. 9A. The user can alternately squeeze and release pressure on the trigger, which reversibly moves slider 125*a* back and forth along slider track 377 to alter the forces pinching the tissue. Once the user is satisfied with the position of the tissue, continued squeezing of the trigger moves components to the configuration shown in FIG. 9C.

Figure 9C:
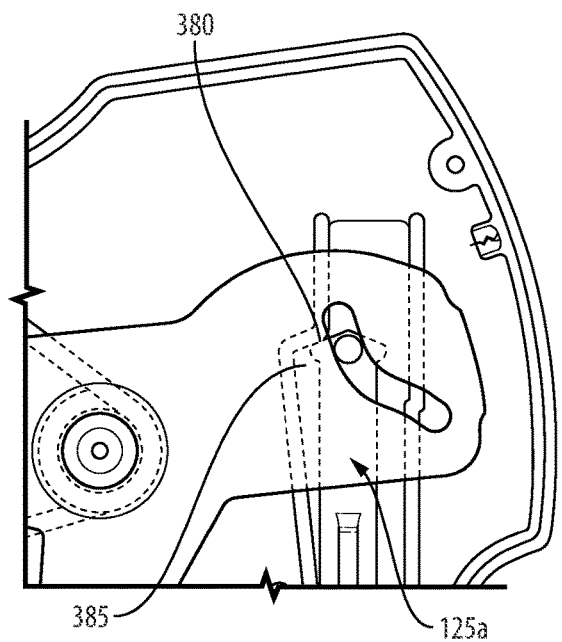

FIG. 9C shows the device of FIG. 9B after the user has moved the trigger to a second position. As the components move from the first position to the second position, the angled surface 380 at the proximal end of the slider 125a enters the latch 385, an angled recessed area in the housing shell. The contact with the cam track forces the slider 125a to slide against the angled surface of the latch to further move the slider distally. This sliding action transfers force to the slider with significant mechanical advantage thus allowing the user squeezing the handle to have significant leverage to force the slider to its maximum distal position.

Figure 9D:
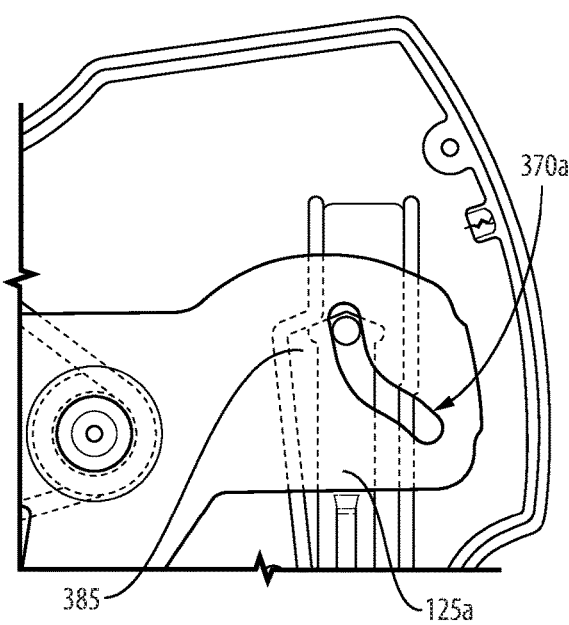

FIG. 9D shows the device of FIG. 9C after the trigger has been fully squeezed. The trigger has rotated but the slider has remained motionless because the curve of the cam track 370a, 370b is configured so that it maintains a holding force to keep the slider 125a in a fixed position in the latch 385. This interrupted motion allows the slider to remain stationary while the trigger continues to rotate. Continued rotation of the trigger deploys the fastener as will be explained with reference to FIG. 10.

Figure 10A:
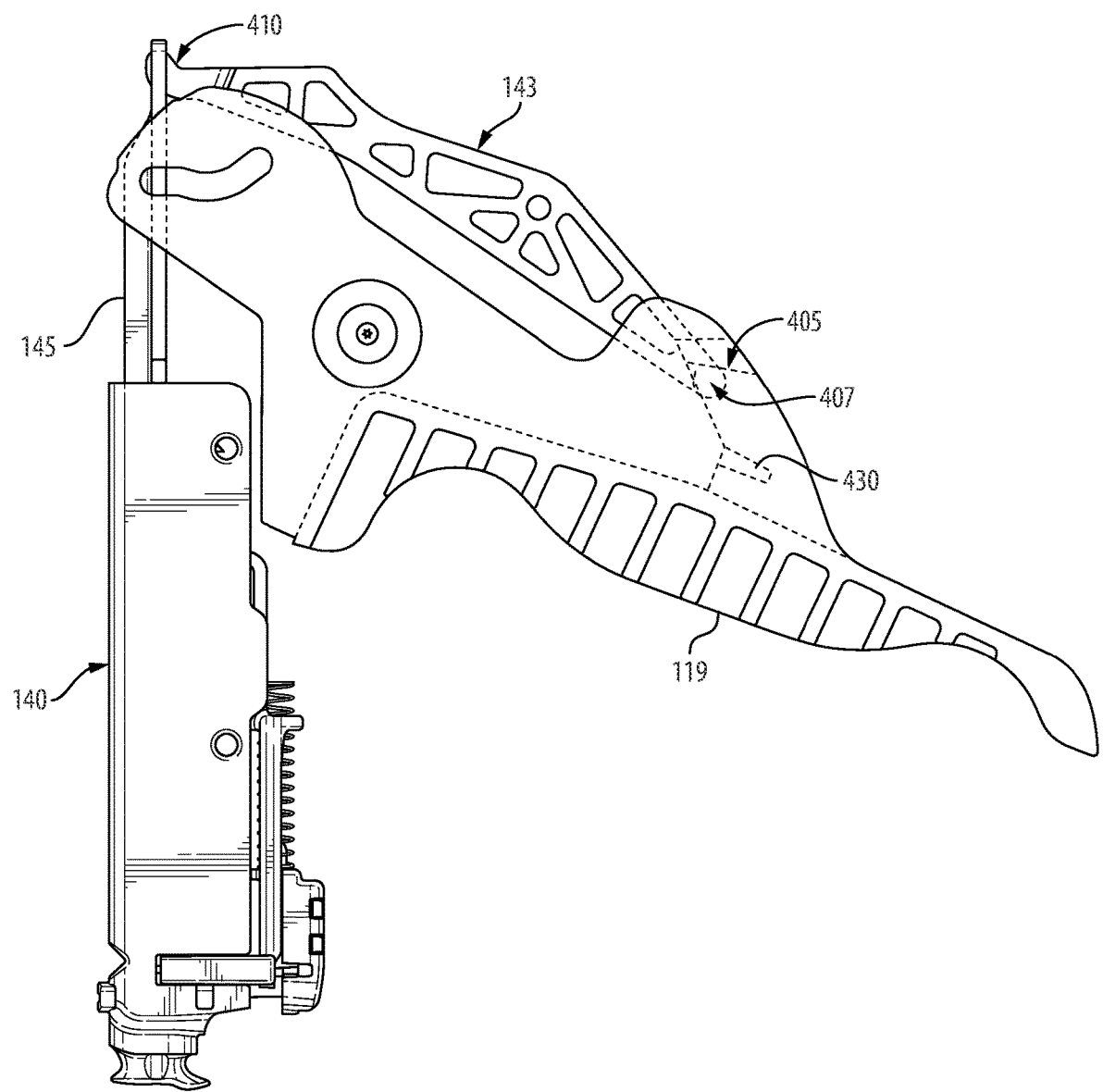
FIGS. 10A, 10B, and 10C show selected components removed from an embodiment of the apparatus to illustrate the movement of the components when the trigger is squeezed by the user.
Figure 10B:
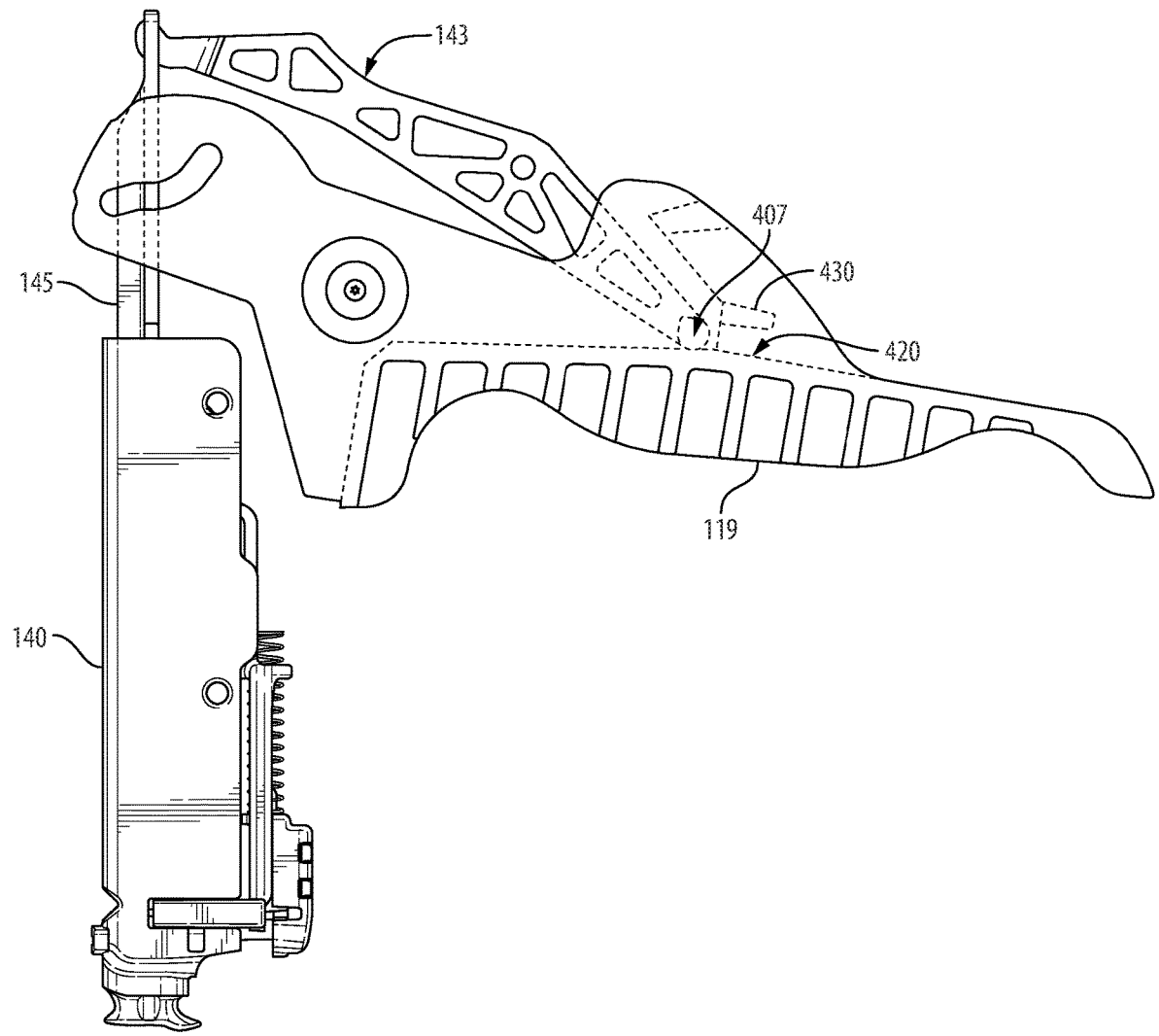
Figure 10C:
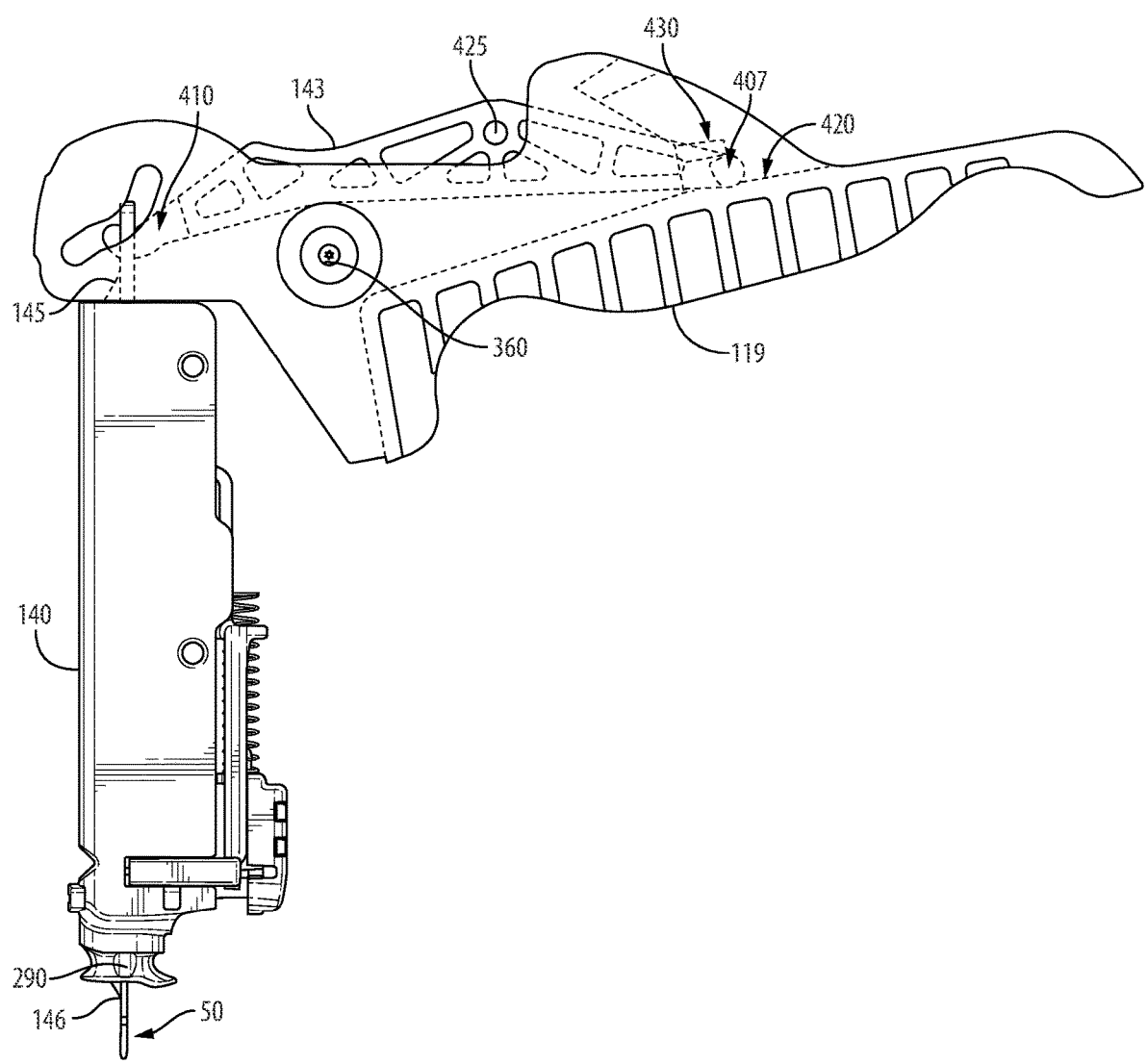

The present invention will be better understood from a description of the components involved in deploying a fastener. Embodiments of these components are shown in FIGS. 10A-10C removed from the device for the purpose of this description. In FIG. 10A the trigger 119, plunger lever 143, and fastener delivery mechanism 140 are shown in their initial positions prior to operation of the device by the user. The plunger keeper 405 contacts the plunger lever pin 407 to maintain the plunger lever 143 in the position shown, for example during shipping and storage. The distal end of the plunger lever referred to as the plunger driver 410 is operatively connected to the plunger needle assembly 145 by a tab-in-slot arrangement or other slidable connections known in the art. The restraining force provided by the plunger keeper 405 is therefore shared with the plunger needle assembly 145 which maintains the internal components of the fastener delivery mechanism 140 in their initial positions. At this point, plunger lifter 430 is not engaged. The action of the plunger lifter 430 is described below.

FIG. 10B shows the components of FIG. 10A after the user has squeezed the trigger 119 to move it to a first position, which corresponds to the position illustrated in FIG. 7A and FIG. 9B. It is important to note that the plunger lever 143 and the plunger needle assembly 145 remain in their initial positions as shown in FIG. 10A. This movement of the trigger 119 to this first position brings the plunger lever pin 407 into contact with the trigger deck 420 but up to this point has not moved the plunger lever 143. This initial rotation to the first position allows the user to release the trigger to reposition the tissue as previously described, without initiating deployment of a fastener from the fastener delivery mechanism 140. The action of the plunger lifter 430 is described below.

FIG. 10C shows the components of FIG. 10B after the user has fully squeezed the trigger 119 to deploy the fastener. The positions of the components correspond to the positions illustrated in FIG. 7C and FIG. 9D. The movement of the trigger 119 to the position shown transfers force from the trigger deck 420 to the plunger lever pin 407 causing the plunger lever 143 to rotate about plunger lever pivot 425. The rotational movement of the plunger lever transfers force from the plunger driver 410 to the plunger needle assembly 145 which acts on the internal components of the fastener delivery mechanism 140 (as described in Rogers). As a result of these actions the insertion device 146 moves through the exit 290 carrying a single fastener 50 for insertion into the tissue. Following deployment of the fastener, the user releases pressure on the trigger and the spring 141 (shown in FIG. 8) returns the trigger to its initial position of FIG. 10A. As the trigger rotates about trigger pivot hole 360 to its initial position, plunger lifter 430 acts on the plunger lever pin 407 to cause rotation of the plunger lever 143 about the plunger lever pivot 425. This rotation of the plunger lever in the reverse direction from its previous actions, lifts the plunger needle assembly 145 thus restoring the internal components of the fastener delivery mechanism and readying it for the next deployment according to the teachings in Rogers.

Figure 11:
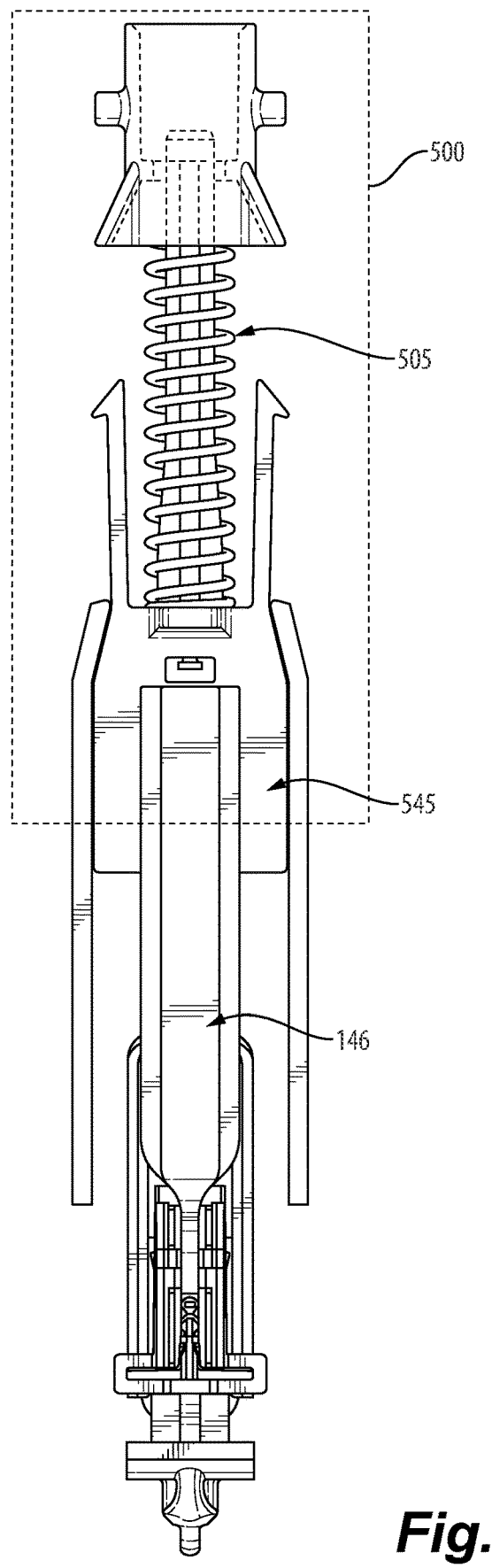
FIG. 11 shows an alternate embodiment of the present invention including additional components.

Another embodiment of the present invention includes additional components contained within the fastener delivery mechanism as shown in FIG. 11. Plunger needle assembly 545 replaces plunger needle assembly 145 to provide an interface to a spring-powered delivery mechanism 500. The insertion device 146, other components of the fastener delivery mechanism, sliders 125a, 125b and tissue holders 130a, 130b (not shown) remain the same as presented heretofore. The additional components of the alternate embodiment allow a driving spring 505 to be compressed in a first phase of fastener deployment and then to be released in a second phase to accelerate the insertion device 146 carrying the fastener. The components contained within the dotted lines of FIG. 11 will be further described with reference to FIGS. 12A-12E.

FIG. 12A shows the position of the components of the spring-powered delivery mechanism 500 at the beginning of the deployment prior to the user operating the device. The driving head 510 is held at the proximal limit of its travel by the driving spring 505 applying force to the retainer ring 512 to hold it against the topper 515 at the most proximal end of the plunger needle assembly 545. The stops, 507a, 507b, are described in detail below.

FIG. 12B demonstrates distal movement of the components relative to the stops 507a, 507b. The stops are molded features with stop 507a on the interior side of the delivery mechanism left housing 147 (see FIG. 3) and stop 507b on the interior side of the delivery mechanism right housing 149 (see FIG. 3) of the fastener delivery mechanism 140 (FIG. 3). As the driving head 510 moves distally in response to the user squeezing the trigger (not shown), the driving spring 505 of spring-powered delivery mechanism 500, which is preloaded with a small force between the retainer ring 512 and the plunger seat 517, forces the plunger needle assembly 545 to move such that all of the components move distally relative to the stops 507a, 507b. Movement to the position indicated in this FIG. 12B allows the plunger needle assembly 545 to pick up one of the plurality of fasteners in the fastener delivery mechanism as described in Rogers. As further illustrated in FIG. 12C, sear-like barbed extensions on the plunger needle assembly, referred to herein as sears 520a, 520b, engage with the stops 507a, 507b.

In FIG. 12C, the sears 520a, 520b are engaged with the stops 507a, 507b to momentarily arrest the movement of the plunger needle assembly 545. As the user continues to squeeze the trigger, the driving head 510 of the spring-powered delivery mechanism 500 moves distally compressing the driving spring 505. The driving head 510 includes sloped surfaces shown here as release cone 525 which interact with the sears 520a, 520b to disengage them from the stops 507a, 507b. The mechanism to release the sear may be a conical surface or simply sloped tabs protruding from the driving head or other shapes known in the art which can interact with the sears to bend them medially and release them from the stops.

FIG. 12D shows the components of the spring-powered delivery mechanism 500 of FIG. 12C after the sears 520a, 520b have disengaged from the stops 507a, 507b. The sears 520a, 520b have released the energy stored in the driving spring 505 and the plunger needle assembly 545 has accelerated distally. In this rapid motion the plunger needle assembly acts on the insertion device 146 to drive the fastener into the tissue as shown in FIG. 7C. At the completion of the fastener deployment the user releases pressure on the trigger and the driving head is pulled proximally as shown in FIG. 12E.

FIG. 12E illustrates the position of the components of the spring-powered delivery mechanism 500 of FIG. 12D as they move toward their starting positions. The topper 515 is engaged with the retainer ring 512 which transfers the proximal pulling force of the driving head 510 to move the plunger needle assembly 545 proximally. As the sears 520a, 520b pass the stops 507a, 507b, the sloped surfaces cause the sears to bend medially to facilitate their movement past the stops. Final proximal movement of the driving head 510 brings all components of the spring-powered deliver mechanism back to the starting position as shown in FIG. 12A.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

While the present invention has been set forth in terms of a specific embodiment or embodiments, it will be understood that the present invention herein disclosed may be modified or altered to other configurations. Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. Accordingly, the invention is not limited only to disclosed details.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A hand-held surgical device for deploying bioabsorbable fasteners to close a wound or incision in tissue, the device comprising:
   a body comprising a handle element including a user-actuatable trigger and a barrel element including a distal end for positioning one or more fasteners relative to a wound or incision in tissue;
   a tissue pinching and folding assembly positioned adjacent to the distal end of the barrel element and operably coupled to the trigger, wherein, upon placement of the distal end of the barrel element relative to a wound or incision and in response to user actuation of said trigger, the tissue pinching and folding assembly is configured to temporarily secure and physically evert opposing edges of the wound or incision relative to the distal end of the barrel element in preparation for deployment of one or more of a plurality of fasteners, wherein the tissue pinching and folding assembly comprises:
      an introducer positioned at, and extending from, the distal end of the barrel element, the introducer comprising an elongate body configured to directly contact opposing edges of the wound or incision; and
      a pair of opposing tissue holder elements positioned at the distal end of the barrel element and on opposing sides of the elongate body of the introducer, each tissue holder comprising a pincer member and a foot member configured to cooperatively move with one another relative to the introducer in response to user actuation of the trigger; and
   a fastener delivery mechanism operably coupled to the trigger and configured to deploy one or more of a plurality of bioabsorbable fasteners from the distal end of the barrel element in response to user actuation of said trigger.

2. The device of claim 1, wherein each of the plurality of fasteners comprises a first leg, a second leg, and a flexible bridge member connecting the first and second legs.

3. The device of claim 1, wherein the fastener delivery mechanism is configured to cause a given fastener to extend outwardly and away from a distal-most end of the tissue pinching and folding assembly and the distal-most end of the barrel and subsequently penetrate opposing edges of the wound or incision such that the fastener is deployed entirely distal to the device and delivered below the surface of the tissue.

4. The device of claim 1, wherein the elongate body of the introducer comprises a pair of pinch rails extending along the opposing sides of the elongate body.

5. The device of claim 4, wherein each tissue holder element comprises a pincer element and a foot element, wherein, in response to user actuation of the trigger, the pincer element is adapted to pinch and secure a portion of a corresponding edge of the wound or incision against a corresponding pinch rail and the foot element is adapted to evert a portion of the corresponding edge of the wound or incision to thereby position an inner surface thereof for subsequent receipt of a portion of a fastener.

6. The device of claim 5, wherein the introducer comprises an exit through which at least a fastener passes during operation of the fastener delivery system in response to user actuation of the trigger.

7. The device of claim 6, wherein the foot element of each tissue holder element is adapted to expose the inner surface of the respective edge of the wound or incision relative to the exit of the introducer such that a deployed fastener passing through the exit is able to bilaterally engage the opposing edges of the wound or incision and thereby hold said edges together.

8. The device of claim 1, wherein the trigger is coupled to the pair of tissue holder elements and the fastener delivery mechanism by way of independent connections allowing for sequential operation thereof.

9. The device of claim 8, wherein:
user actuation of the trigger to an initial first position causes the pincer member of each tissue holder element to rotate inwardly toward the introducer and further pinch and secure a portion of a corresponding edge of the wound or incision against a corresponding side of the introducer;
user actuation of the trigger to a subsequent second position causes the foot member of each tissue holder element to rotate inwardly toward the introducer and further evert a portion of the corresponding edge of the wound or incision to thereby position an inner surface thereof for subsequent receipt of a portion of a fastener; and
user actuation of the trigger to a subsequent third position causes operation of the fastener delivery mechanism resulting in deployment of a fastener to bilaterally engage the opposing edges of the wound or incision and thereby hold said edges together.

10. The device of claim 1, wherein each pincer member comprises one or more sharp protrusions.

11. The device of claim 1, wherein each tissue holder element is injection molded from a single material.

12. The device of claim 11, wherein the pincer member and foot member of each tissue holder element are monolithically formed with one another.

13. The device of claim 1, wherein the pincer member and foot member of each tissue holder element are formed from different materials and assembled to cooperatively form a given tissue holder element.

14. The device of claim 1, wherein the pincer member and foot member are movable relative to one another.

15. The device of claim 1, further comprising a pair of slider elements, each slider element having a proximal end operably coupled to the trigger and a distal end operably coupled to a respective one of the pair of tissue holder elements such that actuation of the trigger causes movement of the pair of slider elements which, in turn, causes corresponding movement of the pair of opposing tissue holder elements.

16. The device of claim 1, wherein the introducer comprises a retraction finger positioned at one end of the elongate body and adapted to engage a first apex of the wound or incision to thereby provide traction opposing forces applied at a second apex of the wound or incision.

17. The device of claim 1, wherein the fastener delivery mechanism is configured to retain a plurality of fasteners and further comprises one or more insertion needles configured to releasably engage and deploy each of the plurality of fasteners in a one-by-one fashion in response to repeated user actuations of the trigger.

18. The device of claim 17, wherein each of the plurality of fasteners comprises a first partially-cannulated leg, a second partially-cannulated leg, and a flexible bridge member connecting the first and second partially-cannulated legs, wherein the first and second partially-cannulated legs are each configured to allow a respective insertion needle to pass within a portion of the partially-cannulated leg.

19. The device of claim 18, wherein the trigger is operably coupled to a plunger-needle assembly, the plunger-needle assembly comprising two insertion needles parallel to each other and configured to pass within a portion of a respective partially-cannulated leg of a fastener, and, in response to user actuation of the trigger, the plunger-needle assembly causes the insertion needles to engage a fastener and thereby cause each leg of the fastener to penetrate opposing edges of the wound or incision thereby inserting the fastener and, in response to user releasing the trigger, the plunger-needle assembly causes the insertion needles to leave the fastener completely distal to the device and below the tissue surface.

20. The device of claim 17, wherein each of the plurality of fasteners comprises a first cannulated leg, a second cannulated leg, and a flexible bridge member connecting the first and second cannulated legs, wherein the first and second cannulated legs are each configured to allow passage therethrough of a respective insertion needle that extends through the cannulated leg with sharp ends exposed distally.

21. The device of claim 20, wherein the trigger is operably coupled to a plunger-needle assembly, the plunger-needle assembly comprising two insertion needles parallel to each other and configured to pass through a respective leg of a fastener.

22. The device of claim 21, wherein, in response to user actuation of the trigger, the plunger-needle assembly causes the insertion needles to engage a fastener and simultaneously penetrate opposing edges of the wound or incision thereby inserting the fastener and, in response to user releasing the trigger, the plunger-needle assembly causes the insertion needles to leave the fastener completely distal to the device and below the tissue surface.

23. The device of claim 21, wherein the fastener delivery mechanism is configured to receive and retain a magazine comprising a plurality of stacked fasteners and the plunger-needle assembly is configured to releasably engage, by way of the pair of insertion needles, the front-most fastener arranged in the stack of fasteners for subsequent deployment.

24. A hand-held surgical device for deploying bioabsorbable fasteners to close a wound or incision in tissue, the device comprising:
a body comprising a handle element including a user-actuatable trigger and a barrel element including a distal end for positioning one or more fasteners relative to a wound or incision in tissue;
a tissue pinching and folding assembly positioned adjacent to the distal end of the barrel element and operably coupled to the trigger, wherein, upon placement of the distal end of the barrel element relative to a wound or incision and in response to user actuation of said trigger, the tissue pinching and folding assembly is configured to temporarily secure and physically evert opposing edges of the wound or incision relative to the distal end of the barrel element in preparation for deployment of one or more of a plurality of fasteners; and
a fastener delivery mechanism operably coupled to the trigger and configured to deploy one or more of a plurality of bioabsorbable fasteners from the distal end of the barrel element in response to user actuation of said trigger, wherein the fastener delivery mechanism comprises a spring-powered delivery assembly comprising:
- a plunger-needle assembly configured to releasably engage a forward-most fastener in a stack of fasteners provided in a magazine;
- a driving head operatively coupled to the trigger and the plunger-needle assembly, wherein the driving head is configured to move the plunger-needle assembly indirectly through actions on a driving spring;
- a stop-mechanism comprising sears configured to engage corresponding stops and thereby arrest movement of the plunger-needle assembly when the driving head is moved to a first driving head position; and
- a release element adapted to disengage the sears from the corresponding stops when the driving head is moved to a second driving head position.

25. The device of claim 24, wherein:
user actuation of the trigger to an initial first position causes the driving head to move to the first driving head position and the plunger-needle assembly to engage the forward-most fastener; and
user actuation of the trigger to a subsequent second position causes the driving spring to compress and the driving head to move to the second driving head position such that, upon disengagement of the sears from the corresponding stops, the plunger-needle assembly is driven via force imparted from the compressed driving spring to thereby deploy and deliver the fastener into tissue at a speed substantially faster than movement of the trigger.

26. The device of claim 24, wherein each of the plurality of fasteners comprises a first leg, a second leg, and a flexible bridge member connecting the first and second legs.

27. The device of claim 24, wherein the fastener delivery mechanism is configured to cause a given fastener to extend outwardly and away from a distal-most end of the tissue pinching and folding assembly and the distal-most end of the barrel and subsequently penetrate opposing edges of the wound or incision such that the fastener is deployed entirely distal to the device and delivered below the surface of the tissue.

\* \* \* \* \*